United States Patent [19]

Imran

[11] Patent Number: 5,327,888
[45] Date of Patent: Jul. 12, 1994

[54] PRECORDIAL ELECTRODE STRIP AND APPARATUS AND METHOD USING THE SAME

[75] Inventor: Mir A. Imran, Palo Alto, Calif.

[73] Assignee: Physiometrix, Inc., Sunnyvale, Calif.

[21] Appl. No.: 893,776

[22] Filed: Jun. 5, 1992

[51] Int. Cl.⁵ ........................................ A61B 5/0402
[52] U.S. Cl. ................................................... 128/640
[58] Field of Search ............................ 128/640, 644

[56] References Cited

U.S. PATENT DOCUMENTS

| | | | |
|---|---|---|---|
| 4,328,814 | 5/1982 | Arkans | 128/640 |
| 4,353,372 | 10/1982 | Ayer | 128/640 |
| 4,522,211 | 6/1985 | Bare et al. | 128/640 |
| 4,583,549 | 4/1986 | Manoli | 128/640 |
| 4,763,659 | 8/1988 | Dunseath, Jr. | 128/644 X |
| 4,763,660 | 8/1988 | Kroll et al. | 128/644 X |
| 4,852,572 | 8/1989 | Nakahashi et al. | 128/640 |
| 4,854,323 | 8/1989 | Rubin | 128/644 |
| 4,957,109 | 9/1990 | Groeger et al. | 128/640 |
| 4,981,141 | 1/1991 | Segalowitz | 128/696 |
| 5,042,481 | 8/1991 | Suzuki et al. | 128/640 |
| 5,191,886 | 3/1993 | Paeth et al. | 128/640 |

*Primary Examiner*—Lee S. Cohen
*Attorney, Agent, or Firm*—Flehr, Hohbach, Test Albritton & Herbert

[57] ABSTRACT

Precordial electrode strip for use on the torso of patients of different sizes comprising an elongate strip of flexible insulating material. A plurality of precordial electrodes are disposed in longitudinally spaced apart positions on the strip. A plurality of precordial leads are carried by the strip. At least one lead is connected to each of said precordial electrodes. A single connector is connected to said precordial leads for making connection to each of said precordial electrodes.

14 Claims, 3 Drawing Sheets

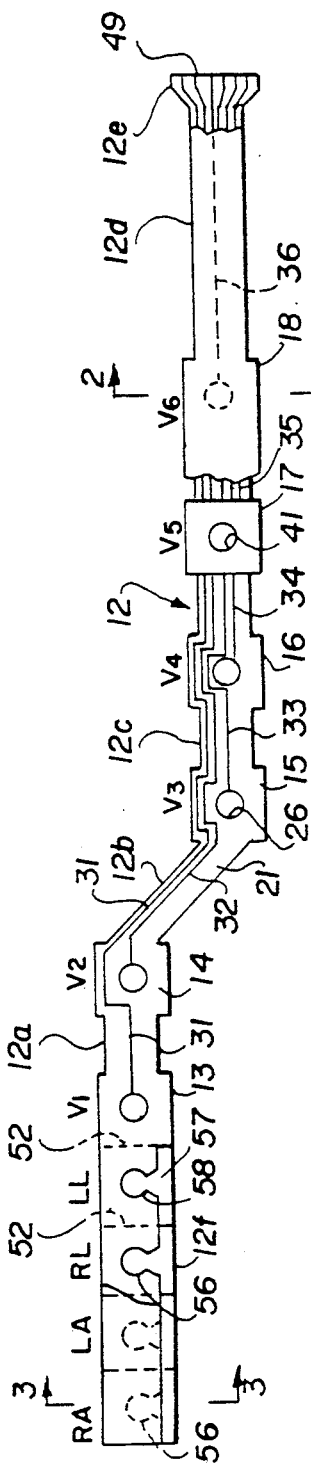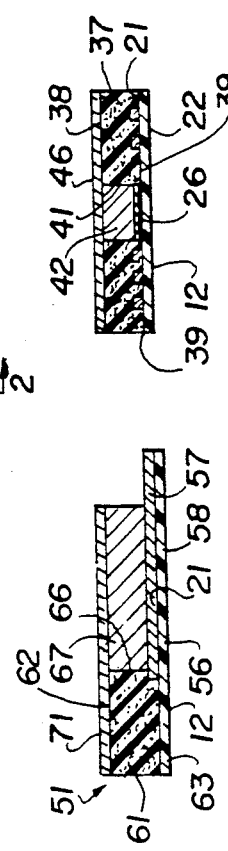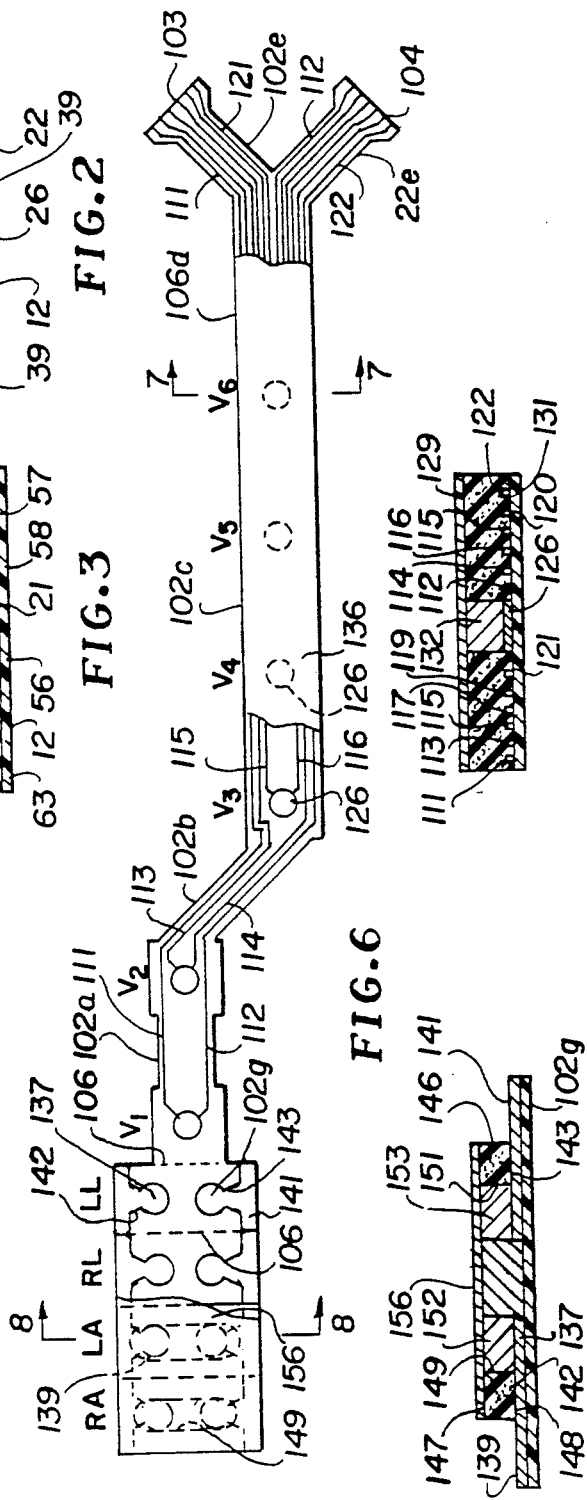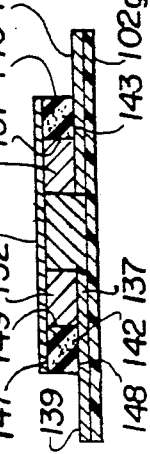

PRECORDIAL ELECTRODE STRIP AND APPARATUS AND METHOD USING THE SAME

FIELD OF THE INVENTION

This invention relates to a precordial electrode strip or array and apparatus and method using the same.

BACKGROUND OF THE INVENTION

In the past, in making electrocardiographic (ECG) measurements in humans it typically has been necessary to individually position six precordial electrodes across the upper chest of the patient and to also place electrodes on the right, arm, left arm, right leg and left leg, for a total of at least ten electrodes, all connected by leads to a conventional ECG apparatus. Errors often occur in connecting these ten electrodes to the ECG apparatus. There is therefore a need for a new and improved apparatus and method for overcoming these disadvantages.

SUMMARY OF THE INVENTION

In general, it is an object of the present invention to provide a precordial strip and apparatus and method utilizing the same for making ECG measurements.

Another object of the invention is to provide a precordial strip which can be utilized on torsos of various sizes.

Another object of the invention is to provide a precordial strip of the above character in which all of the precordial electrodes are carried by a single strip and are connected to a single connector.

Another object of the invention is to provide a precordial strip of the above character which has a minimal effect on X-rays.

Another object of the invention is to provide a strip of the above character which makes it possible to streamline the patient/machine interface.

Additional objects and features of the invention will appear from the following description in which the preferred embodiments are set forth in detail in conjunction with the accompanying drawings.

BRIEF DESCRIPTION OF THE DRAWINGS

FIG. 1 is a plan view showing a precordial strip incorporating the present invention with associated electrodes utilized for making an ECG measurement.

FIG. 2 is a cross-sectional view taken along the line 2—2 of FIG. 1.

FIG. 3 is a cross-sectional view taken along the line 3—3 of FIG. 1.

FIG. 6 is a plan view of another embodiment of a precordial strip incorporating the present invention and associated electrodes for utilization in making redundant ECG measurements in an EP procedure.

FIG. 7 is a cross-sectional view taken along the line 7—7 of FIG. 6.

FIG. 8 is a cross-sectional view taken along the line 8—8 of FIG. 6.

DETAILED DESCRIPTION

Figures 4, 5:
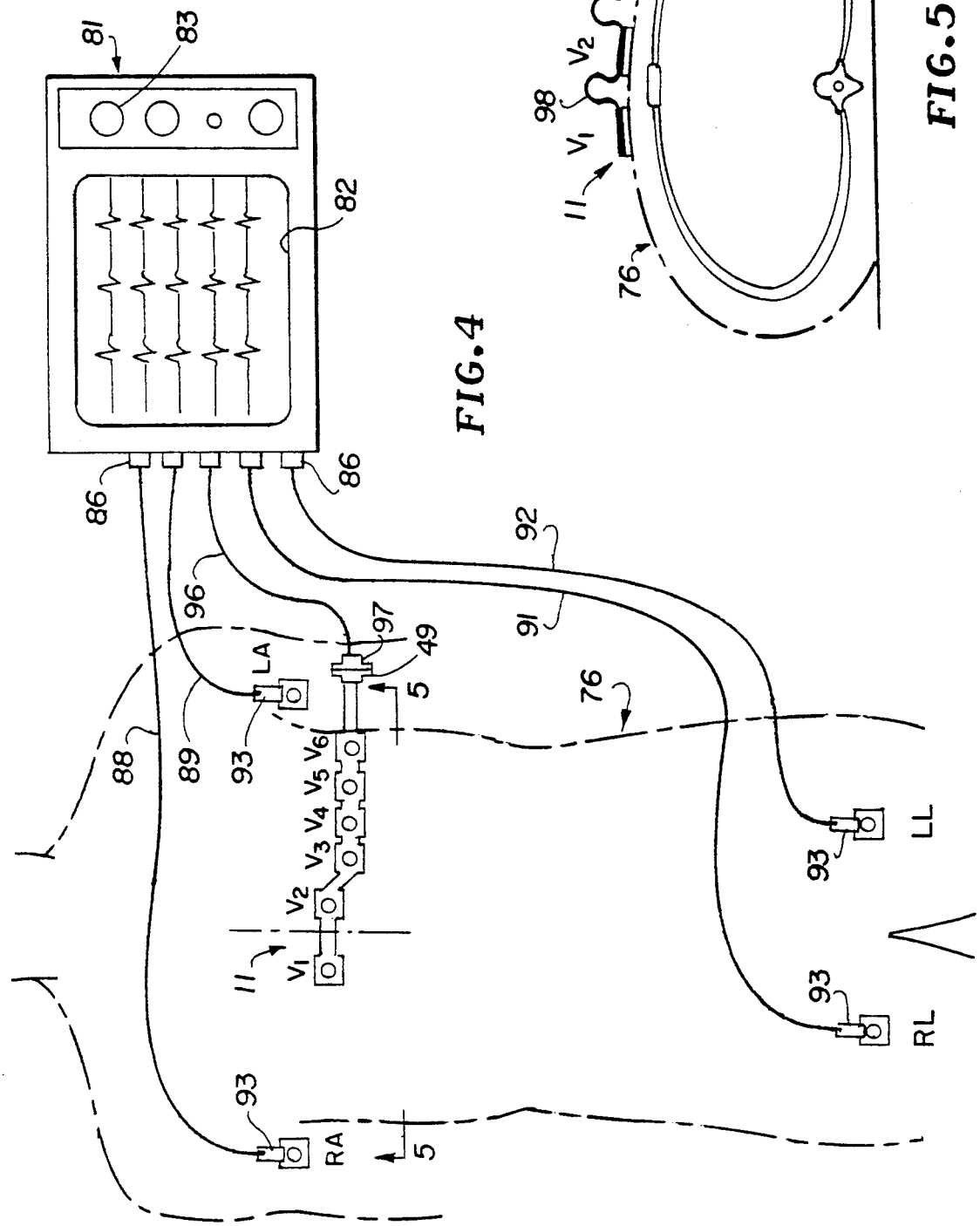
FIG. 4 is a schematic illustration of a patient in a supine position having a precordial electrode strip incorporating the present invention and associated electrodes connected into an ECG apparatus.
FIG. 5 is a cross-sectional view taken along the line 5—5 of FIG. 4 showing the mounting of the precordial strip on the torso.

In general, the precordial strip of the present invention is comprised of an elongate strip of flexible insulating material and a plurality of electrodes are disposed in spaced apart positions on said strip longitudinally on the strip. A plurality of leads are carried by the strip with at least one lead being connected to each precordial electrode. A single connector is connected to the precordial leads.

More in particular, a precordial strip 11 incorporating the present invention is shown in FIGS. 1, 2 and 3. As shown therein, it is utilized for mounting the six precordial electrodes which are conventionally placed around the apex of the heart while making ECG measurements. The precordial strip or array 11 consists of elongate flexible strip 12 formed of a suitable insulating material such as plastic having a thickness of 1-5 mils and a width of ⅛-¾ of an inch One plastic found to be suitable is a polycarbonate. The strip 12 is provided with a straight portion 12a having larger rectangular portion 13 and 14 at opposite ends. The strip is provided with an inclined portion 12b which adjoins the straight portion 12a at one end and adjoins another straight portion 12c at the other end. The straight portion 12c is provided with spaced apart rectangular portions 15, 16, 17 and 18. The strip 12 is also provided with a tail portion 12d which adjoins the portion 12c and enlarged connector portion 12e. The strip 12 is provided with an upper surface 21 and a lower surface 22. The rectangular portion 13 can have a suitable dimension, as for example 1 inch by 1 inch. The portions of the strip 12 between the rectangles can have a suitable width, as for example ¼ inch.

A metal conducting pad 26 is centrally disposed on the upper surface 21 of each of the rectangular portions 13–18. A pattern of traces or conductors also formed of a conducting metal is deposited on the upper surface 21 to provide leads 31–36 which are connected to and formed integral with the metal pads 26 provided on the rectangular portions 13–18, respectively. The leads 31–36 and the metal pad 26 can be fabricated using a conventional flex circuit technology with the metal pads and leads being formed of a suitable conducting metal such as copper. The metal pads and leads are then (1–2 mils) so that they will not leave a shadow on X-ray images. As can be seen, the leads 31–36 extend from the left to the right as viewed in FIG. 1, and terminate on the connector portion 12e so that all six leads are present on this connector portion 12e.

Cutouts 37 in the form of parallelpipeds are provided which have an outer rectangular configuration which generally corresponds to the configuration of the rectangular portions 13–18, and are formed of a suitable insulating foam material such as polyurethane, which are provided with top surfaces 38 and bottom surfaces 39 to which a sticky adhesive (not shown) has been applied. The cutouts 37 are provided with centrally disposed holes 41 which are positioned so that they overlie the metal pads 26 when the cutouts are placed over the rectangular portions 13–18. The holes 41 have a diameter which is greater than the diameter of the metal pads 26.

Cylindrical electrodes 42 are provided in the holes 41 and are formed of a suitable conductive elastomer such as that described in co-pending application Ser. No. 07/745,863 filed Aug. 16, 1991. As can be seen from FIG. 2, the electrodes 42 are generally flush with the top and bottom surfaces 38 and 39 of the cutouts. The cutouts 37 with the electrodes 42 positioned therein are placed over the metal pads 26 so that the electrodes 42 are in contact with the metal pads. The cutouts will adhere to the rectangular portions 13-18 by means of the adhesive carried by the bottom surface 39. The top surfaces 38 are then covered by release liners 46 formed of a suitable material such as paper and are retained on the top surfaces 38 by the adhesive carried by the top surfaces 38. This completes the construction of the precordial electrodes which are designated at V1, V2, V3, V4, V5 and V6, as shown in FIG. 1 of the drawings which are connected to the edge connector 49 by the leads 31-36.

Associated electrodes 51 are provided for the RA, LA, RL and LL electrodes conventionally described as Right Arm, Left Arm, Right Leg and Left Leg electrodes. These electrodes 51 are formed by an extension 12f of the strip 12 which has been provided with longitudinally spaced apart perforations 52 extending transversely across the same so that the electrodes assemblies 51 can be separated from each other and from the precordial strip 11. Thus to provide four of such electrodes 51, three of the said transversely extending sets of perforations 52 are provided, as shown in FIG. 1.

A metallic pad 56 formed of a suitable material such as a layer of copper is provided which is adherent to the top surface 21 of the strip 12. Each pad 58 is connected to a strip 57 extending along one edge of the strip 12f and is connected thereto by a neck 58. The contact 56, the strip 57 and the neck 58 can be formed integral with each other on the top surface 21 of the strip portion 12f, as shown in FIG. 1. Each electrode assembly 51 also includes a cutout 61 formed of an insulating foam material of the type hereinbefore described in connection with the cutouts 37. They are provided with top and bottom surfaces 62 and 63 having a sticky adhesive thereon. As shown, the cutouts 61 have the same general configuration as the cutouts 37. Each cutout is provided with a centrally disposed hole 66 which overlies the pad 56. As can be seen from FIGS. 1 and 3, the cutout 37 does not extend over a portion of the strip 57, so that it remains exposed for making contact therewith as hereinafter described. An electrode 67 is provided which is disposed within the hole 66 and makes contact with the pad 56 and is formed of a suitable conductive elastomer such as described in co-pending application Ser. No. 07/745,863 filed Aug. 16, 1991. Alternatively, the electrode can be formed of a hydrogel or a liquid conductive gel impregnating a sponge insert placed in the hole 66. A release liner 71 formed of a suitable material such as paper is adhered to the top surface 62 of the cutout 61 and, if desired, can be formed as a one-piece release liner 46.

Use of the precordial strip 11 in conjunction with the associated electrode assemblies 51 may now be briefly described as follows. Let is be assumed that it is desired to make an ECG measurement on a patient 76 which is shown in a supine position in FIG. 4. The precordial strip with the associated electrode assemblies 51 are removed from the packaging provided by the manufacturer. The release liner 46 and the release liner 71 can be removed by lifting it off of the cutouts 37 and 61. The four electrode assemblies 51 are separated from each other by tearing along the perforations 52 and then placing them in appropriate locations on the torso of the patient 76. The right arm electrode RA is placed on the right arm, the left arm electrode LA on the left arm, the right leg electrode RL on the right leg, and the left leg electrode LL on the left leg, generally in the positions shown in FIG. 4. The precordial strip 11 is then placed over the precordium, also as shown in FIG. 4. The precordial strip 11 which has the electrodes V1-V6 and the electrodes RA, LA, RL and LL are then connected by conventional means to an ECG apparatus 81 which is provided with a video screen 82 and appropriate controls 83. It is also provided with a plurality of connectors 86 which are connected by insulated cables or conductors 88 and 89 and 91 and 92 which are provided with suitable connectors such as alligator clips 93 well known to those skilled in the art. The clips 93 are clipped to and make contact with the metallic strip 57 provided on each of the electrode assemblies 51. A cable 96 is connected to another of the connectors 86 and is provided with an edge connector 97 which is connected to the edge connector 49 of the precordial strip 11.

When the precordial strip 11 is mounted on the precordium of the patient, the electrodes V1 through V6 can be adjustably positioned on the precordium depending upon the size of the patient. Because the strip 12 is flexible in between the electrodes V1 through V6, it can be bowed upwardly as shown in FIG. 5 between the electrodes to obtain the desired spacing between the electrodes. For large patients, the loops 98 formed between the electrodes can be reduced in size or eliminated to obtain the appropriate spacing. The spacing between the electrodes V1 and V6 is designed so that the precordial strip can be utilized on the largest human being. For smaller human beings, the excess length of strip between the electrodes can be formed into loops as shown in FIG. 5 without affecting the efficacy of the precordial strip.

By utilization of such a precordial strip 11 with the associated electrodes 51, it is possible to greatly reduce the time required for placement of the electrodes on the patient. It also reduces the opportunity for error because the electrodes V1 through V6 on the precordial strip are preconnected so as to eliminate the possible error in making such connections by the technician or nurse performing the ECG procedure.

Another embodiment of the precordial strip and associated electrodes which is particularly useful in making redundant ECG measurements during an electrophysiologystudy is shown in FIGS. 6 and 7 which is provided with redundancy. The precordial strip 101 is provided with the electrodes V1 through V6 and associated electrodes RA, LA, RL and LL. These electrodes are all formed on a strip 102 of a flexible plastic material of the same type as utilized for strip 12. The strip 102 is provided with portions 102a extending between electrodes V1 and V2, portion 102b extending between electrodes V2 and V3 and extending at an angle, as for example 45° with respect to the portion 102a, and a straight portion 102c which carries the electrodes V3 through V6 and extends at a substantial angle, as for example 45° with respect to the section 102b. The section 102c adjoins another straight portion 102d which ends in two angularly extending tail portions 102e and 102f that terminate in edge connectors 103 and 104. The strip also is provided with a portion 102g which adjoins the portion 102a and which is provided with transversely extending perforations 106 to permit separation of the electrodes RA, LA, RL and LL from each other.

The construction of the electrodes V1 through V6 is substantially identical as that for the electrodes V1 through V6 described in FIG. 1, with the exception that each of the electrodes is connected to two conductors with one of each two conductors being provided on the one edge connector 103 and the other of each two conductors being provided on the edge connector 104 so that each electrode is represented by a termination on the edge connector 103, and similarly that each electrode is present on the other connector 104. As shown, the conductors for the one edge connector 103 lie on one side of the strip 101, whereas the conductors for the edge connector 104 lie on an upper level as shown in FIGS. 6 and 7. Thus, the edge connector 103 is connected to odd numbered leads 111 through 121 connected to one side of each of the electrodes V1 through V6, and the edge connector 104 is connected to even numbered conductors 112 through 122 connected to the other sides of the electrodes V1 through V6.

Each of the electrodes V1-V6 includes a metal pad 126 which can be formed in the same manner as the metal pad 26. The pads 126 are connected to the conductors 111 through 122 as hereinbefore described and if desired can be formed integral with the leads 111-122. Rectangular cutouts 127 of the type hereinbefore described are also provided which have centrally disposed holes 128. The cutouts have upper and lower surfaces 129 and 131 which are provided with a sticky adhesive so that the lower surface 131 will adhere to the upper surface of the strip 101. An electrode 132 formed of a conductive elastomer of the type hereinbefore described and as disclosed in co-pending application Ser. No. 07/745,683 filed Aug. 16, 1991, is disposed in each of the holes 128 and is in contact with the pad 126. A release liner 136 is provided for the upper surface 129 and is removably secured thereto.

The additional electrode assemblies for the RA, LA, RL and LL electrodes consist of metallization of the type hereinbefore described for providing for each electrode, a common oval-shaped contact pad 137 which is connected to stripes 139 and 141 by necks 142 and 143. Cutouts 146 are provided which have upper and lower surfaces 147 and 148. Each of the cutouts is provided with an oval-shaped hole 149 which overlies the contact pad 137. Electrodes 152 and 153 are provided in the holes 149 and make contact with the contact pads 137 and the electrodes 152 are formed of a conductive elastomer of the type described in co-pending application Ser. No. 07/745,683 filed Aug. 16, 1991. A release liner 156 covers the electrodes 152 and 153 and is adhered to the sticky upper adhesive surface 147.

Figure 9:
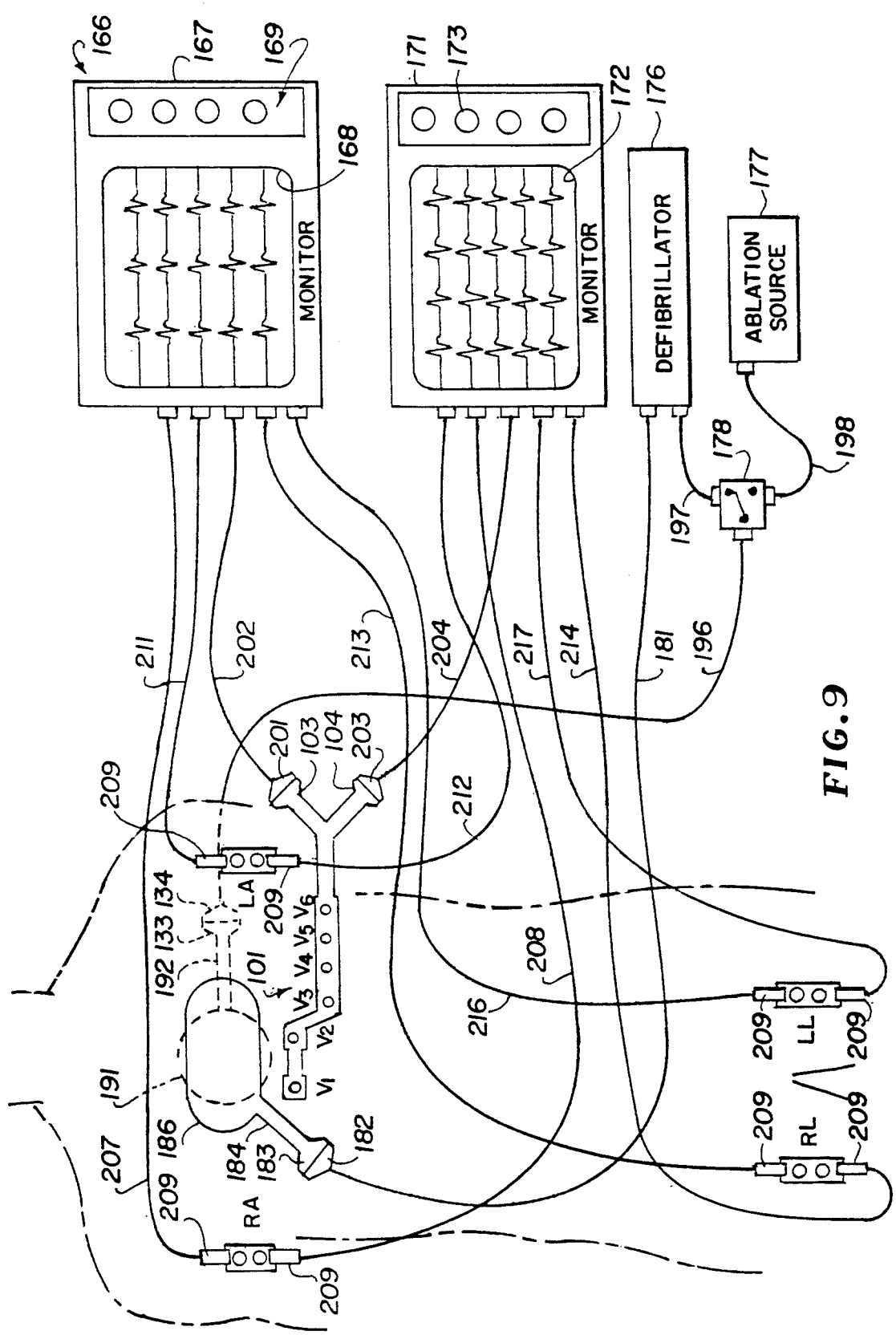
FIG. 9 is a view of a patient in a supine position utilizing the precordial strip and electrodes shown in FIG. 6 connected to an apparatus in an EP procedure.

Operation and use of the precordial strip 101 with the precordial electrodes V1 through V6 and the associated electrodes RA, LA, RL and LL may briefly be described as follows in connection with an electrophysiology study. Electrophysiology (EP) studies are performed on patients suffering from cardiac arrhythmias. Some of these arrhythmias could be lethal. For this reason, the patient's 12-lead surface ECG is typically monitored by two different monitors as a safety precaution. Let it be assumed that the precordial strip or device 101 is to be utilized during an electrophysiology (EP) examination on a patient 161 lying in a supine position as shown in FIG. 9. The electrodes V1-V6 of the precordial strip can be positioned on the precordium in the manner described in conjunction with FIG. 4. Similarly, the electrodes RA, LA, RL and LL can be positioned on the limbs, i.e., the arms and legs of the patient, also in the manner hereinbefore described in conjunction with FIG. 4. The EP apparatus 166 to be utilized therewith is of a conventional type and includes redundant monitoring in the form of a first monitor 167 which is provided with a screen 168 and controls 169, and a second monitor 171 which is provided with a screen 172 and controls 173. It also includes a defibrillator 176 of a conventional type and an ablation source 177 of a suitable type such as one providing radio frequency energy, which are connected through a switch 178. The output of the defibrillator 176 is connected by a cable 181 to a connector 182 which is connected to a connector 183 carried by the tail 184 of a large-surface-area defibrillator pad 186 which is centrally disposed on the chest of the patient 161 slightly above and centered with respect to the electrodes V1 and V2 as shown particularly in FIG. 9. A grounding electrode 191 is provided beneath the supine patient and is generally circular and engages the back side of the patient immediately below the electrode 86. This electrode 191 is connected by cable 192 to a connector 193. The connector 193 is connected to a connector 194 which is connected to a cable 196 that is connected to one terminal of the switch 178. The other two terminals of the switch 178 are connected to the defibrillator 176 by cable 197 and the other terminal is connected to the ablation source 177 by a cable 198.

The precordial electrode strip 101 has its edge connector 103 connected to a connector 201 and is connected by a cable 202 to the monitor 167, and similarly the edge connector 104 is connected to a conductor 203 which is connected by a cable 204 to the monitor 171.

In a similar manner, the monitors 167 and 171 are connected by cables 207 and 208 to the RA electrode on opposite sides by alligator clips 209. Cables 211 and 212 are similarly connected to opposite ends of the LA electrode by the alligator clips 209. Cables 213 and 214 are connected to opposite ends of the RL electrode by alligator clips 209 and are connected to the monitors 167 and 171. Similarly, conductors 216 and 217 by the use of the alligator clips 209 are connected to opposite ends of the LL electrode and to the monitors 167 and 171.

With this apparatus, the physician can alternatively perform ablation and/or defibrillation merely by operation of the switch 178. The precordial electrode strip 101 with the limb electrodes RA, LA, RL and LL make it possible to provide redundant monitoring with only a single set of electrodes. The number of wires or cables leaving the patient and connected to the apparatus are greatly reduced to greatly reduce preparation time, and to also eliminate the possibility of error. In the limb electrodes, the conducting strips are disposed on opposite sides or ends of the electrodes facilitating making connections to the two separate monitors. In such a construction, it is very easy to utilize alligator clips on opposite sides of the electrodes.

In view of the foregoing, it can be seen that there has been provided a precordial electrode strip with associated electrodes which substantially reduces the number of wires from the patient. In turn, as pointed out above, this reduces preparation time and also reduces the possibility of error. The use of tabs which typically interfere substantially with X-rays and cast dark shadows are eliminated. The thin metal strips which are utilized for making connection with alligator clips are off to the sides of the torso and do not interfere with the area of interest, as for example the heart which is being X-rayed. By utilizing dual connectors on the precordial strip, it is possible to eliminate a second set of electrodes which serves to streamline the patient/machine interface, particularly in the "EP" lab.

What is claimed is:

1. In a precordial electrode strip for use on the torso of patients of different sizes, an elongate strip of flexible insulating material, a plurality of precordial electrodes disposed in longitudinally spaced apart positions with respect to said strip so that there are portions of the strip between the electrodes, a plurality of precordial leads carried by the strip, at least one lead being connected to each of said precordial electrodes, and a single connector connected to said precordial leads for making connection to each of said precordial electrodes, said strip being provided with a straight portion, an inclined portion, and another straight portion which is substantially parallel to the first-named straight portion, the precordial electrodes being identified as V1, V2, V3, V4, V5 and V6, the V1 and V2 electrodes being disposed on the first straight portion and the electrodes V3 through V6 being disposed on the second straight portion.

2. A precordial electrode strip as in claim 1 wherein the longitudinal spacing between the precordial electrodes is sufficient to accommodate the largest size patient, said strip between the precordial electrode being flexible so that for smaller size patients the portions of the strip between the electrodes can be formed into loops to permit close spacing of the precordial electrodes.

3. A precordial electrode strip as in claim 1 wherein the leads are in the form of metallic leads adherent to said strip of insulating material.

4. A precordial electrode strip as in claim 1 wherein each of said precordial electrodes is provided with a contact pad with a precordial lead in contact with the contact pad and wherein the electrode also includes a conductive elastomer in contact with and overlying the contact pad.

5. A precordial electrode strip as in claim 4 wherein each of said precordial electrodes includes a cutout formed of an insulating material and having a hole therein in registration with the contact pad and wherein the conductive elastomer is disposed within the hole.

6. A precordial electrode strip as in claim 5 wherein said cutout is provided with first and second surfaces having a sticky adhesive on said first and second surfaces and wherein said second surface is in contact with the strip of flexible insulating material.

7. A precordial electrode strip as in claim 6 together with a release layer secured to the first surface of the cutout.

8. A precordial electrode strip as in claim 1 wherein said single connector is in the form of an edge connector.

9. A precordial electrode strip as in claim 1 together with an additional set of precordial leads carried by the strip of flexible insulating material and connected to said precordial electrodes with another single connector connected to said additional set of precordial leads.

10. A precordial electrode strip as in claim 1 together with additional electrodes, separable means securing said additional electrodes to said precordial strip and forming a part of said precordial strip.

11. A precordial electrode strip as in claim 10 wherein the flexible elongate strip is provided with laterally extending perforations to permit the separation of the electrodes.

12. A precordial electrode strip as in claim 10 wherein said additional electrodes are formed of a flexible material having an upper surface with metallization of the upper surface forming a contact pad and a stripe together with a cutout formed of an insulating material having a hole therein in registration with the contact pad and being a size so that the metallic stripe is exposed, and a conductive elastomer disposed in the hole making contact with the contact pad.

13. A precordial electrode strip as in claim 12 together with a release liner adherent to said cutouts.

14. In a method for making an electrical measurement on a patient by use of a measurement apparatus, utilizing precordial electrodes V1 through V6 and limb electrodes RA, La, RL and LL, placing the V1 through V6 precordial electrodes as a precordial array on the torso of the patient, placing the limb electrodes RA and LA on the right and left arms respectively of the patient, placing the limb electrodes RL and LL on the right and left legs respectively of the patient, connecting the precordial electrodes to the apparatus by use of first and second connections to each of the electrodes V1 through V6 of the precordial array to a single connector and connecting the limb electrodes to the apparatus so that redundant monitoring can be provided.

* * * * *